United States Patent [19]

Mifune et al.

[11] 4,243,739
[45] Jan. 6, 1981

[54] SILVER HALIDE PHOTOGRAPHIC LIGHT-SENSITIVE MATERIAL

[75] Inventors: Hiroyuki Mifune; Shunji Takada; Yoshitaka Akimura; Shigeo Hirano, all of Minami-ashigara, Japan

[73] Assignee: Fuji Photo Film Co., Ltd., Minami-ashigara, Japan

[21] Appl. No.: 83,750

[22] Filed: Oct. 11, 1979

[30] Foreign Application Priority Data

Oct. 12, 1978 [JP] Japan .................................. 53-125602

[51] Int. Cl.$^3$ ........................... G03C 5/30; G03C 1/28
[52] U.S. Cl. .................................... 430/266; 430/444; 430/564; 430/567; 430/599; 430/600; 430/602; 430/603; 430/949
[58] Field of Search ............... 430/600, 603, 599, 564, 430/266, 567, 602, 444, 949

[56] References Cited

U.S. PATENT DOCUMENTS

| | | | |
|---|---|---|---|
| 2,419,975 | 5/1947 | Trivelli | 430/599 |
| 4,030,925 | 6/1977 | Leone et al. | 430/217 |
| 4,116,697 | 9/1978 | Bigelow | 430/599 |

*Primary Examiner*—Mary F. Downey

*Attorney, Agent, or Firm*—Sughrue, Rothwell, Mion, Zinn and Macpeak

[57] ABSTRACT

A silver halide photographic light-sensitive material having at least one silver halide photographic emulsion layer comprising substantially surface latent image type silver halide grains, and containing in said photographic emulsion layer or at least one of other hydrophilic colloid layers a compound represented by the following general formula (I):

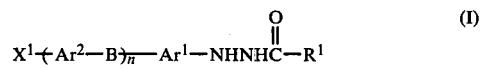

wherein $X^1$ represents a group containing a

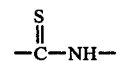

moiety, $Ar^1$ and $Ar^2$ each represents a substituted or unsubstituted aromatic group, B represents a divalent linking group, n is 0 or 1, and $R^1$ represents a hydrogen atom, an unsubstituted alkyl group, or a substituted or unsubstituted aryl group.

30 Claims, No Drawings

SILVER HALIDE PHOTOGRAPHIC LIGHT-SENSITIVE MATERIAL

BACKGROUND OF THE INVENTION

1. Field of the Invention

This invention relates to a silver halide photographic light-sensitive material and, more particularly, to a silver halide photographic light-sensitive material providing photographic properties of extremely contrasty negative gradation.

2. Description of the Prior Art

U.S. Pat. No. 2,419,975 teaches that contrasty negative properties can be obtained by adding a hydrazine compound to a silver halide photographic emulsion. This patent describes that extremely contrasty photographic properties of more than 10 in gamma ($\gamma$) are obtained by adding a hydrazine compound to a silver bromochloride emulsion and developing with a developer having a pH value of as high as 12.8. However, strongly alkaline developers having a pH value near 13 are susceptible to oxidation with air and are therefore too unstable to be stored for a long period of time.

Super-contrasty photographic properties of more than 10 in gamma are extremely useful for the photographic reproduction of images with continuous gradation employing a dot image-forming process which is useful for making printing plates, or for reproduction of line images, irrespective of whether the images are negative or positive. For the purpose of obtaining such photographic properties, a silver chlorobromide emulsion containing more than 50 mol% and preferably more than 75 mol% silver chloride has been used and developed with a hydroquinone-containing developer having an extremely reduced concentration of effective sulfite ion (usually 0.1 mol/l or less). However, such developer is so unstable due to its low sulfite ion concentration that it cannot be stored longer than three days.

In addition, the above-described processes all require a silver chlorobromide emulsion containing silver chloride in a comparatively high content and hence high sensitivity cannot have been obtained. Thus, it has been eagerly desired to obtain super-contrasty photographic properties useful for the reproduction of dot images or line images using a highly sensitive emulsion and a stable developer.

Silver halide photographic emulsions permitting extremely contrasty negative photographic properties using a stable developer have been disclosed in Japanese Patent Application (OPI) Nos. 16623/78 (The term "OPI" as used herein refers to a "published unexamined Japanese patent application"), 20921/78, 20922/78, etc. The acylhydrazine compounds used therein have proved to possess some defects. One is that they undergo serious changes in sensitivity and gradation when stirring of the developer is changed. Light-sensitive materials for use in printing are processed using an automatic developing machine or manual development (dish development). Usually, stirring conditions greatly differ depending upon the developing process and, in addition, stirring methods or stirring strength differ depending upon the kind of the automatic developing machine. Thus, differences in sensitivity and gradation result in photographic materials depending upon the manner in which they are processed. Further, even in the same automatic developing machine, the stirring of the developer is not always uniform but varies from place to place within the developing machine and often results in uneven development when developing large sized film. Therefore, it has strongly been desired to obtain super-contrasty photographic light-sensitive materials which exhibit less variation in sensitivity and gradation even when the developer stirring conditions are changed and which are useful for the reproduction of dot images or line images.

SUMMARY OF THE INVENTION

An object of the present invention is to provide a silver halide photographic light-sensitive material which permits one to obtain an extremely contrasty negative image using a stable developer.

Another object of the present invention is to provide a silver halide light-sensitive material providing an extremely contrasty negative image, which exhibits less change in sensitivity and gradation and less unevenness of development due to changes in conditions such as stirring the developer.

These objects of the present invention are attained by a silver halide photographic light-sensitive material in which at least one silver halide photographic emulsion layer contains substantially surface latent image-forming type silver halide grains, and that photographic emulsion layer or at least one of the other hydrophilic colloid layers making up the material contains a compound represented by the following general formula (I):

(I)

wherein $X^1$ represents a group containing a

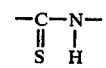

moiety, $Ar^1$ and $Ar^2$ each represents a substituted or unsubstituted aromatic group, B represents a divalent linking group, n represents 0 or 1, and $R^1$ represents a hydrogen atom, or an unsubstituted alkyl or a substituted or unsubstituted aryl group.

DETAILED DESCRIPTION OF THE INVENTION $R^1$ represents a hydrogen atom, a straight chain or branched chain unsubstituted alkyl group having 1 to 3 carbon atoms, or a substituted or unsubstituted aryl group (e.g., a phenyl group). The suitable substituents for the aryl group $R^1$ are a hydroxy group, a carboxy group, a halogen atom (e.g., a chlorine atom, a bromine atom) or a sulfo group. Specific examples of $R^1$ other than hydrogen atom include a methyl group, an ethyl group, an n-propyl group, an isopropyl group, a phenyl group, a 4-chlorophenyl group, a 4-bromophenyl group, a 4-carboxyphenyl group, a 4-sulfophenyl group, a 3,5-dichlorophenyl group, a 2,5-dichlorophenyl group, etc. Of these, a hydrogen atom, a methyl group, and a phenyl group including a substituted phenyl group are preferred with a hydrogen atom being particularly preferred.

Preferred examples of the substituent represented by $X^1$ are

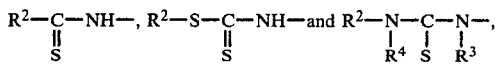

wherein R² represents an aliphatic or aromatic group or a heterocyclic ring, R³ represents a hydrogen atom or an aliphatic group, and R⁴ represents a hydrogen atom or an aliphatic or aromatic group, provided that at least one of R³ and R⁴ represents a hydrogen atom. R² and R³ may combine to form a ring.

Examples of the aliphatic groups represented by R² and R⁴ include a substituted or unsubstituted straight, branched or cyclic alkyl group, an alkenyl ($C_3$–$C_{18}$) group, and an alkynyl ($C_3$–$C_{18}$) group.

Examples of the straight chain and branched chain alkyl groups for R² and R⁴ are, for example, alkyl groups containing 1 to 18 and preferably 1 to 10 carbon atoms and, more specifically, a methyl group, an ethyl group, an isobutyl group, a t-octyl group, etc. Examples of the cycloalkyl groups are, for example, cycloalkyl groups containing 3 to 10 carbon atoms such as a cyclopentyl group, a cyclohexyl group, an adamantyl group, etc. As the substituents for the alkyl groups, there are illustrated an alkoxy ($C_1$–$C_6$) group (e.g., a methoxy group, an ethoxy group, a propoxy group, a butoxy group, etc.), a halogen atom (e.g., chlorine, bromine, fluorine, iodine, etc.), an alkoxycarbonyl group wherein the alkoxy moiety has 1 to 12 carbon atoms, a mono- or bicyclic aryl ($C_6$–$C_{20}$) group (e.g., a phenyl group, a halogen-substituted phenyl group, an alkoxyphenyl group, an alkylphenyl group, etc.), a hydroxy group, a cyano group, a sulfonyl group, etc. Specific examples of substituted alkyl groups represented by R² and R⁴ include a 3-methoxypropyl group, a 4-chlorocyclohexyl group, a benzyl group, a p-methylbenzyl group, a p-chlorobenzyl group, etc.

Examples of the alkenyl group for R² and R⁴ are an allyl group, a butenyl group, etc.

Examples of the alkynyl group for R² and R⁴ are a 2-propynyl group, a 2-butynyl group, etc.

On the other hand, the aromatic groups represented by R² and R⁴ include a substituted or unsubstituted phenyl or naphthyl group. Examples of suitable substituents include an alkyl ($C_1$–$C_{12}$) group, an alkoxy ($C_1$–$C_{12}$) group, an aliphatic or aromatic acylhydrazino ($C_1$–$C_{18}$) group, a dialkylamino ($C_2$–$C_{12}$) group, an alkoxycarbonyl group wherein the alkoxy moiety has 1 to 12 carbon atoms, a cyano group, a carboxyl group, a nitro group, an alkylthio ($C_1$–$C_{18}$) group, a hydroxy group, a sulfonyl group, a carbamoyl group, a halogen atom, etc. As the specific examples of substituted aryl groups represented by R² and R⁴, there are illustrated, for example, a p-methoxyphenyl group, a tolyl group, a p-formylhydrazino group, a p-chlorophenyl group, an m-fluorophenyl group, etc.

The heterocyclic ring represented by R² is a 5- or 6-membered saturated or unsaturated ring containing 1 to 4 hetero atoms such as a nitrogen atom, a sulfur atom or an oxygen atom. As the heterocyclic rings represented by R², there are illustrated, for example, a pyrroline ring, pyridine ring, quinoline ring, indole ring, oxazole ring, benzoxazole ring, naphthoxazole ring, imidazole ring, benzimidazole ring, thiazoline ring, thiazole ring, benzothiazole ring, naphthothiazole ring, selenazole ring, benzoselenazole ring, naphthoselenazole ring, etc.

These hetero rings may be substituted with an alkyl group containing 1 to 4 carbon atoms such as a methyl group or an ethyl group, an alkoxy group containing 1 to 4 carbon atoms such as a methoxy group or an ethoxy group, a mono- or bicyclic aryl group containing 6 to 18 carbon atoms such as a phenyl group, a halogen atom such as a chlorine or bromine atom, etc.

R⁴ is particularly preferably a hydrogen atom.

Aliphatic groups represented by R³ include straight chain, branched chain and cyclic alkyl groups, substituted alkyl groups, an alkenyl group, and an alkynyl group. As the straight chain and branched chain alkyl groups, there are illustrated, for example, alkyl groups containing 1 to 18, preferably 1 to 6, carbon atoms such as a methyl group, an ethyl group, an isopropyl group, etc. As the cycloalkyl groups, there are illustrated, for example, cycloalkyl groups containing 3 to 10 carbon atoms such as a cyclopentyl group, a cyclohexyl group, etc. Examples of substituents include an alkoxy ($C_1$–$C_{12}$) group (e.g., a methoxy group, an ethoxy group, etc.), an aryl ($C_6$–$C_{18}$) group (e.g., a phenyl group, a halogen-substituted phenyl group, an alkoxyphenyl group wherein the alkoxy moiety has 1 to 12 carbon atoms, an alkylphenyl group wherein the alkyl moiety has 1 to 18 carbon atoms, etc.). As the specific examples of substituted groups, there are illustrated a 3-methoxypropyl group, a benzyl group, a p-chlorobenzyl group, a p-methoxybenzyl group, a p-methylbenzyl group, etc. The alkenyl group represented by R³ contains 3 to 12 carbon atoms and is preferably an allyl group or a 2-butenyl group.

R³ preferably represents a hydrogen atom.

When R² and R³ combine to form a ring, the size of the ring is usually 5 - or 6-members. The ring formed by the combination of R² and R³ is a heterocyclic ring capable of absorbing a silver halide (for example, a ring capable of forming a mercapto group by tautomerization) or a heterocyclic ring which can be hydrolyzed during a development processing to convert to a group capable of forming a silver salt. 5-membered rings having the following formulae are preferred:

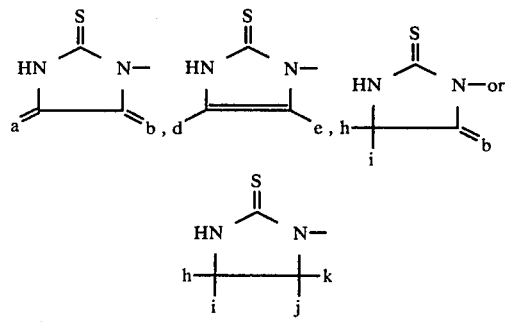

wherein a and b each represents O, S or a divalent group of

and d, e, f, g, h, i, j and k each represents a hydrogen atom, or a straight or branched chain alkyl group having 1 to 18 carbon atoms (e.g., a methyl group, an ethyl group) or a mono- or bicyclic aryl group having 6 to 18 carbon atoms (e.g., a phenyl group) which may be substituted. Preferred specific examples are:

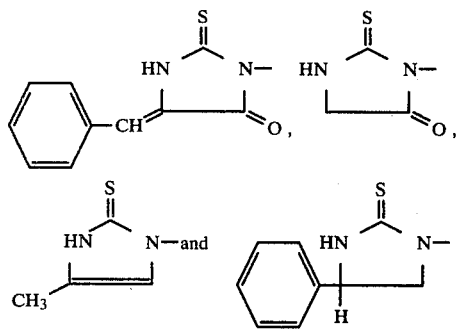

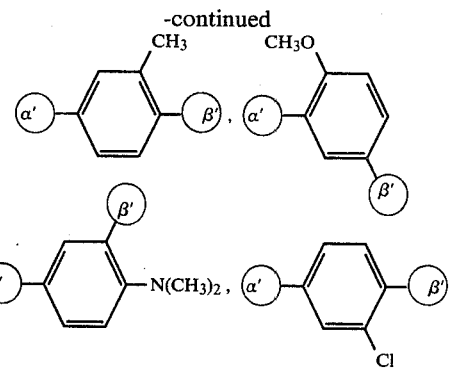

Specific examples of the divalent aromatic groups represented by $Ar^1$ and $Ar^2$ are a substituted or unsubstituted phenylene group or a substituted or unsubstituted naphthylene group. Representative substituents for the aromatic group represented by $Ar^1$ include, for example, an alkyl group containing 1 to 20 carbon atoms (which may be straight chain, branched chain or cyclic), an aralkyl group containing 1 to 3 carbon atoms in the alkyl moiety thereof and 6 to 18 carbon atoms in the aryl moiety thereof (which may be monocyclic or bicyclic), an alkoxy group (preferably containing 1 to 20 carbon atoms), a substituted alkoxy group (preferably containing 1 to 20 carbon atoms where suitable substituents include an alkoxy ($C_1$-$C_{20}$) group, an alkoxycarbonyl ($C_2$-$C_{20}$) group and an acyloxy ($C_2$-$C_{20}$) group and the specific examples of the substituent include a methoxy group and an ethoxy group), an amino group mono- or di-substituted by alkyl or substituted alkyl groups (containing 1 to 20 carbon atoms wherein suitable substituents include an alkoxy ($C_1$-$C_{20}$) group, an alkoxycarbonyl ($C_2$-$C_{20}$) group and an acyloxy ($C_2$-$C_{20}$) group and the specific examples of the substituent include a methyl group, an ethyl group, an n-propyl group and an isopropyl group), an aliphatic acylamino group (preferably containing 2 to 21 carbon atoms), a monocyclic aromatic acylamino ($C_7$-$C_{11}$) group, an alkylthio ($C_1$-$C_{18}$) group, a hydroxy group, etc. As the substituents of the divalent aromatic groups represented by $Ar^2$, there are illustrated, for example, a halogen atom (e.g., chlorine, etc.), a cyano group, an alkoxycarbonyl group wherein the alkoxy moiety has 1 to 12 carbon atoms, a nitro group, a sulfonyl group, a carbamoyl group, etc., in addition to those for $Ar^1$.

Specific examples of $Ar^1$ are, for example:

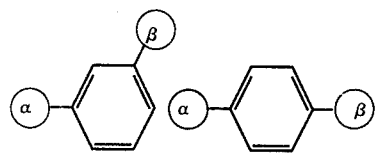

Specific examples of $Ar^2$ are, for example:

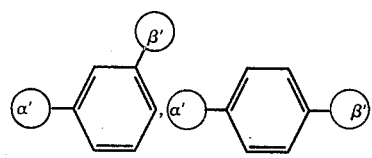

In the above-illustrated formulae, ⓐ-, ⓑ-, ⓐ'-, and ⓑ'- each represents a moiety bound thereto. That is, ⓐ- represents a bond with $X^1$ or B, ⓑ- represents a bond with a hydrazido group, ⓐ'- represents a bond with $X^1$, and ⓑ'- represents a bond with B.

Specific examples of the divalent linking group represented by B are —CONH—, —$SO_2$NH—, —$R^5$—, —$R^5$—O—$R^6$—, $R^5$—S—$R^6$—, —$R^5$—CONH—, —O—$R^5$—CONH—, —S—$R^5$—CONH—, etc., wherein $R^5$ and $R^6$ each represents a divalent aliphatic group including straight and branched chain alkylene groups and cycloalkylene groups which may contain double or triple bonds as well as saturated bonds. $R^5$ and $R^6$ may be the same or different. As the straight and branched chain alkylene groups, there are illustrated, for example, alkylene groups containing 1 to 6 and preferably 1 to 3 carbon atoms such as —$CH_2$—, —$CH_2CH_2$—, —$CH_2CH_2CH_2$—, —$CH(CH_3)$—, —$CH(CH_2CH_3)$—, etc. As the cycloalkylene groups there are illustrated, for example, those containing 3 to 6 carbon atoms such as a 1,2-cyclopropylene group, a 1,4-cyclohexylene group, etc. As the groups containing unsaturated bonds, there are illustrated, for example, those containing a carbon-to-carbon double or triple bond.

Of the compounds represented by the general formula (I), preferred are those wherein $R^1$ represents a hydrogen atom, a methyl group, a phenyl group, or a substituted phenyl group, particularly preferably a hydrogen atom.

Of the compounds of the present invention represented by the general formula (I), those wherein $X^1$ represents

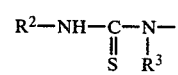

are partly described in Japanese Patent Application (OPI) No. 20318/78. However, in the invention disclosed in the above publication the compounds are used as a "nucleus-imparting agent" providing developing nuclei when applied to an internal latent image-forming type emulsion, that is, to directly obtain positive images by fogging silver halide in unexposed portions. On the other hand, in the present invention the compounds of the general formula (I) are used to increase contrast by using them in combination with a surface latent image-forming type emulsion. That is, they are used to obtain super-contrasty negative images by their action on silver halide in exposed areas. Therefore, the present invention and Japanese Patent Application (OPI) No. 20318/78 are different from each other in terms of the function and effect of the compounds and in the objects and construction of the inventions.

Specific examples of the compounds of the present invention represented by the general formula (I) are as follows. These examples are not to be construed as limiting.

(1) 1-Formyl-2-[4-(3-phenylthioureido)phenyl]hydrazide
(2) 1-Formyl-2-[3-(3-phenylthioureido)phenyl]hydrazide
(3) 2-[4-(3-Ethylthioureido)phenyl]-1-formylhydrazide
(4) 2-[4-(3-allylthioureido)phenyl]-1-formylhydrazide
(5) 1-Acetyl-2-[4-(3-benzylthioureido)phenyl]hydrazide
(6) 2-[4-(3-Ethoxycarbonylmethylthioureido)phenyl]-1-formylhydrazide
(7) 1,3-Bis[4-(2-formylhydrazino)phenyl]thiourea
(8) 1-Benzoyl-2-{4-[3-(4-chlorophenyl)-1-methylthioureido]phenyl}hydrazide
(9) 2-[4-(3-Phenylthioureido)phenyl]-1-trifluoroacetylhydrazide
(10) 1-Formyl-2-{4-[3-(3-phenylthioureido)benzamido]phenyl}-hydrazide
(11) 1-Formyl-2-{4-[4-(3-phenylthioureido)benzamido]phenyl}-hydrazide
(12) 1-Formyl-2-{4-[3-(3-(4-methoxyphenyl)thioureido)-benzamido]phenyl}hydrazide
(13) 1-Formyl-2-{3-[4-(3-phenylthioureido)benzamido]phenyl}-hydrazide
(14) 2-{4-[2-(2,4-di-t-amylphenoxy)-5-(3-ethylthioureido)-benzamido]phenyl}-1-formylhydrazide
(15) 1-Formyl-2-{4-[3-(3-phenylthioureido)benzenesulfonamido]phenyl}hydrazide
(16) 1-Formyl-2-{4-[2-morpholino-5-(3-phenylthioureido)-benzenesulfonamido]phenyl}hydrazide
(17) 2-{4-[2-(4-(3-ethylthioureido)phenoxy)acetamido]-phenyl}-1-formylhydrazide
(18) 1-Formyl-2-{4-[2-(4-(3-phenylthioureido)phenoxy)-propionamido]phenyl}hydrazide
(19) 2-{4-[2-(3-(3-t-butylthioureido)phenylthio)acetamido]-phenyl}-1-formylhydrazide
(20) 1-(4-Chlorobenzoyl)-2-{4-[3-(4-(3-cyclohexylthioureido)phenyl)propionamido]phenyl}hydrazide
(21) 1-Formyl-2-[4-(S-methyldithiocarbamido)phenyl]-hydrazide
(22) 2-[4-(S-Benzyldithiocarbamido)phenyl]-1-formyl-hydrazide
(23) 1-Acetyl-2-{4-[3-(S-allyldithiocarbamido)benzamido]phenyl}hydrazide
(24) 1-Formyl-2-(4-thiobenzamidophenyl)hydrazide
(25) 1-Formyl-2-[4-(4-methoxythiobenzamido)phenyl]-hydrazide
(26) 1-Acetyl-2-(3-thioacetamidophenyl)hydrazide
(27) 2-[4-(3-Cyclohexanethiocarboxamidobenzamido)-phenyl]1-formylhydrazide
(28) 1-Formyl-2-[4-(4-thiopivaloamidobenzenesulfonamido)phenyl]hydrazide
(29) 3-[4-(2-Formylhydrazino)phenyl]-5-phenyl-2-thiohydantoin
(30) 1-[4-(2-Formylhydrazino)phenyl]-4-methyl-2-imidazolinethione The compounds of the general formula (I) used in the present invention can generally be synthesized according to the following processes.

1-Formyl-2-(4- or 3-nitrophenyl)hydrazide or a corresponding 1-acyl-2-(4- or 3-nitrophenyl)hydrazide can be obtained by reacting formic acid or the corresponding acid anhydride or acid chloride with 4- or 3-nitrophenylhydrazine. That is, the reaction is carried out in a molar ratio of the hydrazine to the formic acid, acid anhydride or acid chloride of about 1/1 to 1/5; using a solvent (e.g., ethanol, acetonitrile, etc.) in a concentration of the reactants of about 0.1 to 10 mol/l; at a reaction temperature of about 20° to 100° C.; and under atmospheric pressure. The resulting nitrophenylhydrazides can readily be converted to corresponding amino derivatives by catalytic reduction in a solvent of alcohol (e.g., ethanol, methyl cellosolve, etc.) or dioxane using palladium-on-carbon as a catalyst or by heating with reduced iron in alcohol.

Compounds of the general formula (I) represented by the formula:

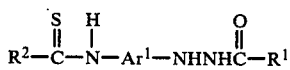

can be obtained by reacting the above-described amines with various esters (e.g., methyl ester, phenyl ester, carboxymethyl ester, etc.) of an aliphatic dithiocarboxylic acid (e.g., dithioacetic acid, etc.) or an aromatic dithiocarboxylic acid (e.g., dithiobenzoic acid, etc.). The reaction is carried out in a molar ratio of the amine to the ester of dithiocarboxylic acid of about 1/1 to ½; using a solvent (e.g., water, ethanol, dioxane or a mixture thereof) in a concentration of the reactants of about 0.1 to 10 mol/l; at a reaction temperature of about 20° to 100° C.; and under atmospheric pressure.

Compounds of the general formula (I) represented by the formula:

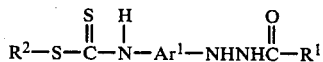

can be synthesized by reacting the above amine with carbon disulfide in the presence of a base such as sodium hydroxide or tertiary amine using alcohol (e.g., methanol, ethanol, etc.) or ether (e.g., dioxane, etc.) as a solvent, and reacting the resulting dithiocarbamate anion with various halides (e.g., methyl iodide, allyl bromide, etc.). The reaction is carried out in a molar ratio of the amine to the carbon disulfide of about 1/1 to ½; using a solvent (e.g., methanol, ethanol, dioxane, etc.) in a concentration of the reactants of about 0.1 to 10 mol/l; at a reaction temperature of about $-10°$ to 50° C.; and under atmospheric pressure.

Compounds of the general formula (I) represented by the formula:

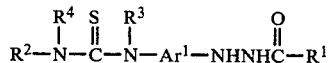

can be obtained by reacting the above amine with an aryl isothiocyanate (e.g., phenyl isothiocyanate, etc.) or an alkyl or alkenyl isothiocyanate (e.g., allyl isothiocyanate, ethyl isothiocyanate, etc.). The reaction is carried out at a molar ratio of the amine to the aryl isothiocyanate of about 1/1 to ½; using a solvent (e.g., ethanol, dioxane and acetonitrile) n a concentration of the reactants of about 0.1 to 10 mol/l; at a reaction temperature of about 0° to about 100° C.; and under atmospheric pressure.

Compounds of the general formula (I) wherein $R^2$ and $R^3$ combine to form a ring can be synthesized by reacting the above-described amine with a sulfur-containing compound such as thiocyanic acid salt or carbon disulfide and a bifunctional compound necessary to form a ring (e.g., chloroacetone, ethyl chloroacetate, etc.). The reaction is carried out at a molar ratio of the amine to the sulfur-containing compound of about 1/1 to ⅕; using a solvent (e.g., ethanol) in a concentration of the reactants of 0.1 to 10 mol/l; at a reaction temperature of about −20° to 100° C.; and under atmospheric pressure.

Compounds of the general formula (I) represented by the formula:

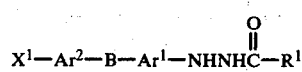

can be obtained by reacting the above-described amine with an acid chloride containing a benzene ring substituted by a nitro group at the 4- or 3-position (examples of the acid chloride are benzoyl chloride, benzenesulfonyl chloride, phenylfatty acid chloride, phenoxyfatty acid chloride, phenylthiofatty acid chloride, etc.) in the presence of an acid removing agent (e.g., triethanolamine, pyridine, etc.) to prepare a corresponding nitro compound (wherein the reaction is carried out at a molar ratio of the amine to the acid chloride of about 1/1 to 1/5; using a solvent (e.g., acetonitrile, dioxane and tetrahydrofuran) in a concentration of the reactants of about 0.1 to 10 mol/l; at a reaction temperature of about 0° to 100° C.; and under atmospheric pressure), converting the nitro compound to amino compound through the above-described catalytic reduction or by using reduced iron, and converting the resulting amino compound to corresponding compound by one of the above-processes.

Synthesis examples of starting materials for the compounds of the present invention and the compounds of the present invention are specifically set forth below.

I. Synthesis of Starting Material (1) 1-Formyl-2-(4-nitrophenyl)hydrazide 459 g of 4-nitrophenylhydrazine was added to 1.6 liters of acetonitrile. Then, 322 g of formic acid was gradually added thereto to prepare a uniform solution. Crystals were precipitated after 20 minutes. After the reaction was conducted for 2 hours at an inside temperature of 80° C., the mixture was cooled and crystals were collected by filtration, washed with acetonitrile, and dried to obtain 493 g of 1-formyl-2-(4-nitrophenyl)-hydrazide having a melting point of 184°–186° C.

(2) 2-(4-Aminophenyl)-1-formylhydrazide 30 g of 1-formyl-2-(4-nitrophenyl)hydrazide was subjected to catalytic reduction in 1,600 ml of ethanol using palladium-on-carbon as a catalyst at a room temperature. The reaction solution was filtered, and the filtrate was evaporated to dryness to obtain 20.5 g of a white solid of 2-(4-aminophenyl)-1-formylhydrazide having a melting point of 123°–125° C.

(3) 1-Formyl-2-(3-nitrophenyl)hydrazide 430 g of 1-formyl-2-(3-nitrophenyl)hydrazide was obtained by reacting 3-nitrophenylhydrazide in the same manner as in (1). m.p. 168°–169° C.

(4) 1-Formyl-2-(3-aminophenyl)hydrazide 21.0 g of 1-formyl-2-(3-aminophenyl)hydrazide having a melting point of 108°–113° C. was obtained by reacting 1-formyl-2-(3-nitrophenyl)hydrazide in the same manner as in (2).

(5) 1-Benzoyl-2-(4-nitrophenyl)hydrazide 30 g of 4-nitrophenylhydrazine and 45 g of benzoic acid anhydride were dissolved in 200 ml of benzene and heated for 3 hours under reflux. The reaction solution was added to ice-water and the product thus formed was collected by filtration, washed with ethanol, and dried to obtain 40 g of 1-benzoyl-2-(4-nitrophenyl)hydrazide having a melting point of 194°–196° C.

(6) 2-(4-Aminophenyl)-1-benzoylhydrazide 22 g of 2-(4-aminophenyl)-1-benzoylhydrazide having a melting point of 135°–137° C. was obtained by catalytically reducing 1-benzoyl-2-(4-nitrophenyl)hydrazide in the same manner as in (2).

(7) 1-Formyl-2-[4-(3-nitrobenzamido)phenyl]hydrazide 68.2 g of 2-(4-aminophenyl)-1-formylhydrazide and 60 ml of triethylamine were dispersed in 500 ml of acetonitrile, and 70 g of 3-nitrobenzoyl chloride was dropwise added thereto while keeping the inside temperature at lower than 50° C. while stirring. Thus, crystals were precipitated. After heating for 2 hours at 60° C., the reaction mixture was cooled and poured into water. Crystals thus formed were collected by filtration, and recrystallized from ethanol to obtain 72.8 g of 1-formyl-2-[4-(3-nitrobenzamido)phenyl]-hydrazide having a melting point of 185°–187° C.

(8) 1-Formyl-2-[4-(3-nitrobenzenesulfonamido)phenyl]hydrazide 15.1 g of 2-(4-aminophenyl)-1-formylhydrazide and 14 ml of triethylamine were dispersed in 50 ml of acetonitrile, and 22.1 g of 3-nitrobenzenesulfonyl chloride dissolved in 50 ml of acetonitrile was dropwise added thereto at room temperature while stirring. After heating for 2 hours at 60° C., the reaction mixture was cooled and poured into water. Crystals thus formed were collected by filtration to obtain 15 g of 1-formyl-2-[4-(3-nitrobenzenesulfonamido)phenyl]hydrazide having a melting point of 188° to 191° C.

(9) 1-Formyl-2-{4-[3-(4-nitrophenoxy)propionamido]-phenyl}-hydrazide 127 g of 3-(4-nitrophenoxy)propionic acid and 120 g of thionyl chloride were reacted for 30 minutes by heating under reflux. After removal of excess thionyl chloride by azeotropic distillation with benzene, the reaction mixture was added to a mixture of 75.5 g of 2-(4-aminophenyl)-1-formylhydrazide, 61 g of triethylamine, and 600 ml of acetonitrile while keeping the inside temperature at lower than 10° C. After the reaction for 2 hours at room temperature, the reaction mixture was stirred for 30 minutes at 50° C., then cooled and poured into water. Crystals thus formed were collected by filtration and recrystallized from ethanol to obtain 120 g of 1-formyl-2-{4-[3-(4-nitrophenoxy)propionamido]-phenyl}hydrazide having a melting point of 117°–118° C. (decomposition).

(10)
1-Formyl-2-{4-[2-(3-nitrophenoxy)acetamido]phenyl}-hydrazide 150 g of thionyl chloride was reacted with 102 g of 2-(3-nitrophenoxy)acetic acid for 1 hour by heating under reflux. After removal of excess thionyl chloride by azeotropic distillation with benzene, the reaction solution was added to a mixture of 75.5 g of 2-(4-aminophenyl)-1-formylhydrazide, 60 g of triethylamine, and 600 ml of acetonitrile while keeping the temperature at lower than 10° C. After being stirred for 1 hour at 50° C., the reaction solution was cooled and poured into water. Crystals thus formed were collected by filtration and recrystallized from ethanol to obtain 61.8 g of 1-formyl-2-{4-[2-(3-nitrophenoxy)acetamido]phenyl}hydrazide having a melting point of 163°–165° C. (decomposition).

II. Synthesis of the Compounds of the Present Invention

(11) Synthesis of Compound 25

6.8 g of 2-(4-aminophenyl)-1-formylhydrazide and 10 g of carboxymethyl-4-methoxydithiobenzoate were dispersed in 80 ml of water, and 1.6 g of sodium hydroxide dissolved in 20 ml of water was dropwise added thereto under stirring while cooling with ice. Further, when the reaction was conducted at room temperature, the reaction solution once became uniform, then yellow crystals were precipitated. The crystals thus formed were collected by filtration, washed with water, and recrystallized from acetone-hexane to obtain 9 g of the end product having a melting point of 206°–212° C.

(12) Synthesis of Compound 21

22.7 g of 2-(4-aminophenyl)-1-formylhydrazide was dissolved in 150 ml of methanol, and 15.7 g of triethylamine was dropwise added thereto while cooling with ice. Then, 11.8 g of carbon disulfide was dropwise added thereto while keeping the inside temperature at lower than 10° C. After the reaction mixture was stirred for 2 hours at room temperature, 22 g of methyl iodide was added dropwise thereto under cooling with ice. After being reacted for 1 hour at 0° C., the reaction solution was further stirred for 2 hours at room temperature, then poured into 600 ml of water. Crystals thus formed were recrystallized from 500 ml of methanol to obtain 21 g of the end product having a melting point of 144° C. (decomposition).

(13) Synthesis of Compound 1

30.2 g of 2-(4-aminophenyl)-1-formylhydrazide was dissolved in 300 ml of methanol and, at 50° C., 32.5 g of phenyl isocyanate was dropwise added thereto in 10 minutes. The reaction mixture immediately heated up, and slightly yellow crystals were precipitated. After being reacted for 30 minutes at 50° C., the reaction mixture was cooled to 20° C. with ice. Crystals thus precipitated were collected by filtration and washed three times with methanol. The resulting crude crystals were dissolved in 170 ml of dimethylformamide, then 1 liter of isopropyl alcohol was added thereto to again precipitate crystals. Crystals thus formed were collected by filtration and washed with isopropyl alcohol to obtain 43 g of the end product having a melting point of 195° C.

(14) Synthesis of Compound 10

800 ml of isopropanol, 80 ml of water, a slight amount of ammonium chloride, and 12 g of 1-formyl-2-[4-(3-nitrobenzamido)phenyl]hydrazide were mixed, and heated over a steam bath under stirring. Then, 80 g of iron dust was added thereto, followed by refluxing the mixture for 1 hour. The reaction solution was filtered, and 11 g of phenyl isocyanate was added to the filtrate, followed by maintaining it at 50° C. for 3 hours. Then, the reaction solution was poured into the same quantity of water. Crystals thus precipitated were collected by filtration. Recrystallization from acetonitrile yielded 8.4 g of the end product having a melting point of 186°–187° C.

(15) Synthesis of Compound 13

18 g of 1-formyl-2-[3-(4-nitrobenzamido)phenyl]hydrazide synthesized according to the process (7), 300 ml of isopropyl alcohol, 60 ml of water, and a slight amount of ammonium chloride were heated. Then, 30 g of iron dust was added thereto, followed by heat-refluxing the mixture for 40 minutes. The reaction solution was filtered, and 13.5 g of phenyl isothiocyanate was added to the filtrate and reacted for 2 hours at 50° to 60° C. Crystals thus formed were collected by filtration, and recrystallized from a mixture solvent of 80 ml of dimethylformamide and 80 ml of water to obtain 19 g of the end product having a melting point of 181°–182° C.

(16) Synthesis of Compound 15

To a mixture of 8.4 g of iron dust, 0.8 g of ammonium chloride, 150 ml of isopropyl alcohol, and 15 ml of water was added 5.0 g of 1-formyl-2-[4-(3-nitrobenzenesulfonamido)phenyl]hydrazide under heat-refluxing. After being heat-refluxed for further 20 minutes, the reaction solution was filtered. 4.1 g of phenyl isothiocyanate was added to the filtrate, and reacted for 2 hours at 45° C. After the reaction mixture was cooled, 150 ml of water was added thereto to separate a gum-like material. After decantation, purification through silica gel column chromatography (developing solvent: ethyl acetate) yielded 4.5 g of the end product as a glassy solid.

(17) Synthesis of Compound 17

500 ml of methyl cellosolve, 50 ml of water, 7 g of ammonium chloride, and 16.5 g of 1-formyl-2-{4-[2-(4-nitrophenoxy)acetamido]phenyl}hydrazide were mixed, and heated over a steam bath under stirring. 70 g of reduced iron was added thereto, and stirred for 4 hours under heat-refluxing. The reaction solution was filtered, and 8.7 g of ethyl isocyanate was added to the filtrate, followed by reacting at 60° to 70° C. for 3 hours. After being cooled, the reaction solution was poured into 3 l of water. Crystals thus precipitated were collected by filtration, and washed with methanol. Recrystallization from acetonitrile yielded 4 g of the end product having a melting point of 177°–178° C. (decomposition).

(18) Synthesis of Compound 31

6.0 g of 2-(4-aminophenyl)-1-formylhydrazide was dissolved in 40 ml of methanol and, at 25° C., 3.9 g of chloroacetone was added thereto in 2 minutes. After the mixture was stirred for further 3 hours at 25° C., 3.6 g of sodium thiocyanate was added thereto, and reacted for 30 minutes at the same temperature, then for 1 hour at 60° C. After concentration of the reaction solution, the concentrate was purified through silica gel column chromatography (developing solvent: ethyl acetate) to obtain 2.5 g of the end product having a melting point of 207°–210° C. (decomposition).

Other compounds can be synthesized by analogy to the above-described processes.

In the case of incorporating the compound of the present invention represented by the general formula (I) in a photographic light-sensitive material, it can be incorporated in one or more of the hydrophilic colloid layers of the light-sensitive material. It may be added to photographic light-sensitive emulsion layers or to other nonlight-sensitive layers such as a protective layer, interlayer, filter layer, antihalation layer, etc. Preferably, it is incorporated in a surface latent image type silver halide photographic emulsion layer.

The compound of the formula (I) is incorporated in the light-sensitive material in an amount of about $10^{-8}$ mol to $10^{-2}$ mol, preferably about $10^{-6}$ to $10^{-3}$ mol, per mol of silver halide in the light-sensitive material. An optimal amount of the compound depends upon the grain size of the silver halide emulsion, the halide composition, the process and the degree of chemical sensitization, the relation between the layer containing the compound and the photographic emulsion layers, the antifogging agent, and the like. Testing methods for the selection of an optimum amount are well known and do not require an undue amount of experimentation.

In order to incorporate the compound of the general formula (I) in silver halide emulsion layers or other nonlight-sensitive hydrophilic colloid layers, the compound is added to photographic emulsions or coating solutions of nonlight-sensitive layers. Specifically, the compound is added to a hydrophilic colloid solution as a solution of a water-miscible organic solvent such as an alcohol (e.g., methanol, ethanol, etc.), ethers (e.g., ethyl acetate, etc.), a ketone (e.g., acetone, etc.), or the like; or, when the compound is water-soluble, as an aqueous solution.

In the case of adding the compound to a photographic emulsion, the addition may be conducted at any stage from initiation of chemical ripening to prior to coating but, preferably, it is conducted after completion of chemical ripening. In particular, addition to a solution which is otherwise ready for coating is preferred.

In the present invention, silver halide grains used in at least one silver halide emulsion layer are preferably substantially surface latent image type grains. The term "substantially surface latent image type" as used herein means that when developed a light-sensitive material which does not contain a compound represented by the general formula (I) of the present invention according to surface-developing process (A) and internally developing process (B) described below, after exposure for 1 to 1/100 second, the sensitivity obtained by surface development (A) is greater than that obtained by internal development (B). The sensitivity obtained by the process (A) is preferably five times or more greater than the sensitivity obtained by the process (B). Sensitivity as used herein is defined as follows:

$$S = \frac{100}{Eh}$$

wherein S represents sensitivity, and Eh represents the exposure amount necessary for obtaining a density just intermediate maximum density ($D_{max}$) and minimum density ($D_{min}$) [i.e., $\frac{1}{2}(D_{max}+D_{min})$].

Surface Development (A)

Development for 10 minutes at 20° C. in a developer having the following formulation.

| | |
|---|---|
| N-Methyl-p-aminophenol (hemisulfate) | 2.5 g |
| Ascorbic Acid | 10 g |
| Sodium Metaborate Tetrahydrate | 35 g |
| Potassium Bromide | 1 g |
| Water to make | 1 l |

Internal Development (B)

Treatment for 10 minutes at about 20° C. in a bleaching solution containing 3 g/l potassium ferricyanide and 0.0125 g/l phenosafranine, then development for 10 minutes at 20° C. in a developer having the following formulation after washing with water for 10 minutes.

| | |
|---|---|
| N-Methyl-p-aminophenol (hemisulfate) | 2.5 g |
| Ascorbic Acid | 10 g |
| Sodium Metaborate Tetrahydrate | 35 g |
| Potassium Bromide | 1 g |
| Sodium Thiosulfate | 3 g |
| Water to make | 1 l |

The above surface developer and internal developer are only developers for testing whether a silver halide emulsion is a surface latent image type or an internal latent image type emulsion, and they are not developers recommended for the development of the light-sensitive material of the present invention.

As silver halide, any of silver chloride, silver chlorobromide, silver chlorobromoiodide, silver bromide, and silver bromoiodide can be used. With silver bromoiodide or silver chlorobromoiodide, the content of silver iodide is preferably not more than 10 mol%.

Since the process of the present invention enables the use of such a wide variety of silver halides, much higher sensitivity can be obtained as compared with conventional processes using "lith" type development.

The photographic emulsion used in the present invention can be prepared according to the processes described in P. Glafkides, *Chimie et al Physique Photographique* (published by Paul Montel in 1967), G. F. Duffin, *Photographic Emulsion Chemistry* (The Focal Press, 1966), V. L. Zelikman et al., *Making and Coating Photographic Emulsion* (published by The Focal Press in 1964), etc.

That is, silver halide emulsions prepared according to any of an acid process, neutral process, and ammoniacal process may be used.

As the manner of reacting a soluble silver salt with a soluble halide, any of a one-side mixing process, a simultaneously mixing process, or combinations thereof, etc., may be employed. It is also possible to employ the process of forming grains in the presence of excess silver ion (a so-called reverse-mixing process). As one of the simultaneous mixing processes, a process of maintaining pAg of the liquid phase, in which silver halide is formed, at a constant level, i.e., so-called controlled double jet process, can be used. This process provides a silver halide emulsion containing silver halide grains having a regular crystal form and an approximately uniform particle size.

Silver halide grains in the photographic emulsion used in the present invention may have a comparatively broad grain size distribution but, preferably, have a narrow grain size distribution. Particularly preferably, 90% (by weight or number) of the total silver halide grains are within ±40% of the mean grain size. Such emulsions are generally called monodisperse emulsions. The mean particle size of the silver halide grains used in the present invention is not particularly limited but, preferably, it is not greater than 0.7μ. The method for determining the mean particle size is described in detail in C. E. K. Mees & T. H. James, *The Theory of the Photographic Process*, 3rd Ed., pp. 36–43 (published by Macmillan Co. in 1966).

A mean particle size of not more than 0.4μ is more preferred in the present invention. The process of the present invention is characterized in that it provides high sensitivity in spite of the small mean particle size of the silver halide grains.

The silver halide grains in the photographic emulsion may be regular crystals such as cubic or octahedral crystals, or irregular crystals such as spherical or plate-like crystals as well as mixed forms thereof. Further, they may comprise a mixture of grains with various crystal forms. The inner part and exterior part of the silver halide grains may be different phases or they may comprise a single homogeneous phase. Two or more silver halide emulsions separately prepared may also be mixed and used.

During the formation of physical ripening of silver halide grains, cadmium salts, zinc salts, lead salts, thallium salts, iridium salts or complex salts, rhodium salts or complex salts, iron salts or complex salts, etc., may be allowed to copresent in the system.

As the binder or protective colloid for the photographic emulsion, gelatin is advantageously used. Also, other hydrophilic colloids can be used. For example, there can be used gelatin derivatives; graft polymers of gelatin and other high polymers; proteins such as albumin, casein, etc.; cellulose derivatives such as hydroxyethyl cellulose, carboxymethyl cellulose, cellulose sulfate, etc.; sugar derivatives such as sodium alginate, starch derivative, etc.; various synthetic and hydrophilic homo- or copolymers such as polyvinyl alcohol, partly acetallized polyvinyl alcohol, poly-N-vinyl pyrrolidone, polyacrylic acid, polymethacrylic acid, polyacrylamide, polyvinylimidazole, polyvinylpyrazole, etc.

As the gelatin, acid-processed gelatin may be used as well as lime-processed gelatin. Further, hydrolyzates or enzyme-decomposed products of gelatin may be used. As gelatin derivatives, those obtained by reacting gelatin with various compounds such as acid halides, acid anhydrides, isocyanates, bromoacetic acid, alkanesultones, vinylsulfonamides, maleinimides, polyalkylene oxides, epoxy compounds, etc., may be used. Specific examples thereof are described in U.S. Pat. Nos. 2,614,928, 3,132,945, 3,186,846, 3,312,553, British Pat. Nos. 861,414, 1,033,189, 1,005,784, Japanese Patent Publication No. 26845/67, etc.

As examples of aforesaid gelatin graft polymer, those prepared by grafting to gelatin a mono- or copolymer of vinyl series monomer such as acrylic acid, methacrylic acid, the derivative thereof such as the esters or amides, acrylonitrile, styrene, etc., may be used. Of these, graft polymers with a polymer having a compatibility with gelatin to some extent such as a polymer of acrylic acid, methacrylic acid, acrylamide, methacrylamide, hydroxyalkyl methacrylate, etc., are preferred. Examples thereof are described in U.S. Pat. Nos. 2,763,625, 2,831,767, 2,956,884, etc.

Typical synthetic hydrophilic high molecular materials are described in, for example, West Germam Patent Application (OLS) No. 2,312,708, U.S. Pat. Nos. 3,620,751, 3,879,205, and Japanese Patent Publication No. 7561/68.

The silver halide emulsion used in the present invention preferably does not contain more than 250 g binder per mol of silver halide. Where the silver halide emulsion contains not more than 250 g binder per mol of silver halide, extremely contrasty photographic properties which are the object of the present invention can be obtained more easily.

The emulsion is usually subjected to the step of removing soluble salts after formation of the precipitate or physical ripening. Noodle washing method which is well known and conducted following gelling gelatin, or a flocculation method utilizing an inorganic salt comprising polyvalent anion such as sodium sulfate, an anionic surfactant, an anionic polymer (e.g., polystyrenesulfonic acid, etc.), or a gelatin derivative (e.g., aliphatically acylated gelatin, aromatically acylated gelatin, aromatically carbamoylated gelatin, etc.) may be employed for the purpose. This step of removing soluble salts may be omitted.

The silver halide emulsion used in the present invention is preferably chemically sensitized but may not be. As methods for chemically sensitizing silver halide emulsion, there are known sulfur sensitization, reduction sensitization, and noble metal sensitization, and any of these may be used alone or in combination. These methods are described in the aforesaid books by Glafkides or by Zelikman et al, or in *Die Grundlagen der photographischen Prozesse mit Silberhalogeniden* compiled by H. Frieser (Alkademische Verlagsgesellschaft, 1968).

Of the noble metal-sensitizing methods, a gold-sensitizing method is typical which uses gold compounds, mainly gold complexes. Complexes of other noble metals than gold such as platinum, palladium, iridium, etc., may be used as well. Specific examples are described in U.S. Pat. No. 2,448,060, British Pat. No. 618,061, etc.

As the sulfur sensitizing agents, there can be used various sulfur compounds such as thiosulfates, thioureas, thiazoles, rhodanines, etc., as well as sulfur compounds contained in gelatin. Specific examples are described in U.S. Pat. Nos. 1,574,944, 2,278,947, 2,410,689, 2,728,668, 3,501,313, 3,656,955, etc.

As the reduction sensitizing agents, there can be used stannous salts, amines, formamidinesulfinic acid, silane compounds, etc. Specific examples thereof are described in U.S. Pat. Nos. 2,487,850, 2,518,698, 2,983,609, 2,983,610, and 2,694,637.

In the light-sensitive material of the present invention, various compounds for preventing fog or stabilizing the photographic properties during production steps, storage, or photographic processing of the light-sensitive material may be incorporated. Many compounds known as antifogging or stabilizing agents such as azoles (e.g., benzothiazolium salts, nitroindazoles, nitrobenzimidazoles, chlorobenzimidazoles, bromobenzimidazoles, mercaptothiazoles, mercaptobenzothiazoles, mercaptobenzimidazoles, mercaptothiadiazoles, aminotriazoles, benzotriazoles, nitrobenzotriazoles, mercaptotetrazoles (particularly, 1-phenyl-5-mercaptotetrazole), etc.); mercaptopyrimidines; mercaptotriazines; thioketo compounds (e.g., oxazolinethione, etc.); azaindenes (e.g., triazaindenes, tetrazaindenes (particularly, 4-hydroxy-substituted 1,3,3a,7-tetrazaindenes, etc.), pentazaindenes, etc.); benzenethiosulfonic acid; benzenesulfinic acid; benzenesulfonamide; etc., may be added. Of these, benzotriazoles (e.g., 5-methylbenzotriazole) are particularly preferred. These compounds may be incorporated in a processing solution.

Addition of a small amount of iodide (e.g., potassium iodide) to the emulsion after formation of the grains, before or after chemical ripening, or before coating enhances the effects of the present invention. Such iodides are suitably added in an amount of $10^{-4}$ to $10^{-2}$ mol/mol Ag.

The photographic emulsion used in the present invention may be spectrally sensitized with methine dyes, or the like. Suitable dyes include cyanine dyes, merocyanine dyes, complex cyanine dyes, complex merocyanine dyes, holopolar cyanine dyes, hemicyanine dyes, styryl dyes, hemioxonol dyes, etc. Particularly useful dyes are those belonging to cyanine dyes, merocyanine dyes, and complex merocyanine dyes. These dyes may contain as basic heterocyclic nucleus any of nuclei usually used for cyanine dyes, that is, there can be contained pyrroline nucleus, oxazoline nucleus, thiazoline nucleus, pyrrole nucleus, oxazole nucleus, thiazole nucleus, selenazole nucleus, imidazole nucleus, tetrazole nucleus, pyridine nucleus, etc.; nuclei wherein an alicyclic hydrocarbon ring or rings are fused to these nuclei; and nuclei wherein an aromatic hydrocarbon ring or rings are fused to these nuclei, i.e., indolenine nucleus, benzindolenine nucleus, indole nucleus, benzoxazole nucleus, naphthoxazole nucleus, benzothiazole nucleus, naphthothiazole nucleus, benzoselenazole nucleus, benzimidazole nucleus, quinoline nucleus, etc. These nuclei may be substituted on the carbon atom or atoms thereof.

Merocyanine dyes or complex merocyanine dyes contain, as ketomethylene structure-containing nucleus, 5- to 6-membered heterocyclic nucleus such as a pyrazolin-5-one nucleus, thiohydantoin nucleus, 2-thiooxazolidine-2,4-dione nucleus, thiazolidine-2,4-dione nucleus, rhodanine nucleus, thiobarbituric acid nucleus, or the like.

Useful sensitizing dyes are described in, for example, German Pat. No. 929,080, U.S. Pat. Nos. 2,231,658, 2,493,748, 2,503,776, 2,519,001, 2,912,329, 3,656,959, 3,672,897, 3,694,217, British Patent No. 1,242,588, Japanese Patent Publication No. 14030/69, etc.

These sensitizing dyes may be used alone or in combination. Combination of sensitizing dyes is often used for attaining, in particular, super-sensitization. Typical examples thereof are described in U.S. Pat. Nos. 2,688,545, 2,977,229, 3,397,060, 3,522,052, 3,527,641, 3,617,293, 3,628,964, 3,666,480, 3,679,428, 3,703,377, 3,769,301, 3,814,609, 3,837,862, British Pat. No. 1,344,281, Japanese Patent Publication No. 4936/48, etc.

Dyes which themselves do not show a spectrally sensitizing action or materials which do not substantially absorb visible light, showing super-sensitivity, may be incorporated in the emulsion together with the sensitizing dyes. For example, aminostilbenes substituted by a nitrogen-containing heterocyclic group (for example, those described in U.S. Pat. No. 2,933,390 and 3,635,721), aromatic organic acid-formaldehyde condensates (for example, those described in U.S. Pat. No. 3,743,510), cadmium salts, azaindene compounds, etc., may be incorporated. Combinations described in U.S. Pat. Nos. 3,615,613, 3,615,641, 3,617,295, and 3,635,721 are particularly useful.

The light-sensitive material of the present invention may contain water-soluble dyes as filter dyes or for various purposes like anti-irradiation. Such dyes include oxonol dyes, hemioxonol dyes, styryl dyes, merocyanine dyes, cyanine dyes, and azo dyes. Of these, oxonol dyes, hemioxonol dyes, and merocyanine dyes are useful. Specific examples of usable dyes are described in British Patents No. 584,609, 1,177,429, Japanese Patent Application (OPI) Nos. 85130/73, 99620/74, 114420/74, U.S. Pat. Nos. 2,274,782, 2,533,472, 2,956,879, 3,148,187, 3,177,078, 3,247,127, 3,540,887, 3,575,704, 3,653,905 and 3,718,472.

The light-sensitive material used in the present invention may contain inorganic or organic hardeners. For example, chromium salts (e.g., chromium alum, chromium acetate, etc.), aldehydes (e.g., formaldehyde, glyoxal, glutaraldehyde, etc.), N-methylol compounds (e.g., dimethylolurea, methyloldimethylhydantoin, etc.), dioxane derivatives (e.g., 2,3-dihydroxydioxane, etc.), active vinyl compounds (e.g., 1,3,5-triacryloylhexahydro-s-triazine, bis(vinylsulfonyl)methyl ether, etc.), active halogen compounds (e.g., 2,4-dichloro-6-hydroxy-s-triazine, etc.), mucohalogenic acids (e.g., mucochloric acid, mucophenoxychloric acid, etc.), isoxazoles, dialdehydo-starch, 2-chloro-6-hydroxytriazinyl gelatin, etc., can be used alone or in combination. Specific examples thereof are described in U.S. Pat. Nos. 1,870,354, 2,080,019, 2,726,162, 2,870,013, 2,983,611, 2,992,109, 3,047,394, 3,057,723, 3,103,437, 3,321,313, 3,325,287, 3,362,827, 3,539,644, 3,543,292, British Pat. Nos. 676,628, 825,544, 1,270,578, German Pat. Nos. 872,153, 1,090,427, Japanese Patent Publication Nos. 7133/59, 1872/71, etc.

The light-sensitive material of the present invention may contain various known surface active agents for various purposes such as coating aid, antistatic purpose, improvement of sliding property, emulsified dispersion, anti-adhesive purpose, and improvement of photographic properties (e.g., acceleration of development, increase in contrast, sensitization, etc.). For example, there can be used nonionic surface active agents such as saponin (steroid series), alkylene oxide derivatives (e.g., polyethylene glycol, polyethylene glycol/polypropylene glycol condensate, polyethylene glycol alkyl or alkylaryl ether, polyethylene glycol esters, polyethylene glycol sorbitan esters, polyalkylene glycol alkylamine or amides, polyethylene oxide adducts of silicone, etc.), glycidol derivatives (e.g., alkenylsuccinic acid polyglyceride, alkylphenol polyglyceride, etc.), fatty acid esters of polyhydric alcohols, sugar alkyl esters, urethanes, ethers, etc.; anionic surface active agents containing acidic groups (such as carboxy group, sulfo group, phospho group, sulfuric ester group, phosphoric ester group, etc.) such as triterpenoid series saponin, alkylcarboxylic acid salts, alkylsulfonic acid salts, alkylbenzenesulfonic acid salts, alkylnaphthalenesulfonic acid salts, alkylsulfuric esters, alkylphosphoric esters, N-acyl-N-alkyltaurines, sulfosuccinic esters, sulfoalkylpolyoxyethylene alkylphenyl ethers, polyoxyethylene alkylphosphates, etc.; amphoteric surface active agents such as amino acids, aminoalkylsulfonic acids, aminoalkylsulfuric or phosphoric esters, alkylbetaines, amineimides, amine oxides, etc.; and cationic surface active agents such as alkylamines, aliphatic or aromatic quaternary ammonium salts, heterocyclic quaternary ammonium salts (e.g., pyridinium, imidazolium, etc.), aliphatic or hetero ring-containing phosphonium or sulfonium salts, etc. In the process of the present invention, imagewise exposed silver halide photographic light-sensitive materials are preferably carried out in the presence of polyalkylene oxide or a derivative thereof.

The polyalkylene oxide or the derivative thereof used in the present invention has a molecular weight of at least about 600, and may be employed either in the silver halide light-sensitive material or in the developer.

The polyalkylene oxide compounds used in the present invention include condensates between polyalkylene oxides comprising at least 10 units of an alkylene oxide having 2 to 4 carbon atoms such as ethylene oxide, propylene-1,2-oxide, butylene-1,2-oxide, preferably ethylene oxide, and compounds having at least one active hydrogen atom such as water, aliphatic alcohols, aromatic alcohols, fatty acids, organic amides, organic amines, hexitol derivatives, etc., and block copolymers of two or more polyalkylene oxides. More specifically, suitable polyalkylene oxide compounds which can be used include polyalkylene glycols, polyalkylene glycol alkyl ethers, polyalkylene glycol aryl ethers, polyalkylene glycol alkylaryl ethers, polyalkylene glycol esters, polyalkylene glycol fatty acid amides, polyalkylene glycol amines, polyalkylene glycol block copolymers, polyalkylene glycol graft polymers, etc.

The number of polyalkylene oxide chains is not limited and one, two or more chains may be present in the molecule. In such a case, each polyalkylene oxide chain may contain less than 10 alkylene oxide units, but the sum of the alkylene oxide units in the molecule must be at least 10. With compounds containing two or more polyalkylene oxide chains in the molecule, each polyalkylene oxide chain may contain the same alkylene oxide units or alkylene oxide units different from that of the other chain or chains. For example, one chain may comprise ethylene oxide units, and the other chain may comprise propylene oxide units. The polyalkylene oxide compounds used in the present invention preferably contain 14 to 100 alkylene oxide units.

Specific examples of polyalkylene oxide compounds which can be used in the present invention are described in Japanese Patent Publication No. 104012/77.

In adding the polyalkylene oxide compound to a silver halide emulsion, it can be added as an aqueous solution of a suitable concentration or as an organic solution by dissolving the polyalkylene oxide compound in a water-miscible organic solvent having a low boiling point at an appropriate stage before coating, preferably after chemical ripening of the silver halide emulsion. The polyalkylene oxide compound may be added to a non-light-sensitive hydrophilic colloid layer such as an interlayer, a protective layer, a filter layer, etc., instead of the silver halide emulsion, if desired.

In addition, in adding the above-described polyalkylene oxide compound to a developer, it can be added to the developer as a solid or as an aqueous solution of a suitable concentration, or by dissolving the polyalkylene oxide compound in a water-miscible low-boiling organic solvent.

A suitable amount of the polyalkylene oxide compound used in the present invention when employed in the light-sensitive material is about $5 \times 10^{-4}$ g to 5 g, preferably $1 \times 10^{-3}$ g to 1 g, per mol of silver halide.

A suitable amount of the polyalkylene oxide compound used in the present invention when employed in a developer is about $1 \times 10^{-2}$ g to 40 g, preferably $5 \times 10^{-2}$ g to 20 g, per liter of the developer.

Specific examples of these surface active agents are described in U.S. Pat. Nos. 2,240,472, 2,831,766, 3,158,484, 3,210,191, 3,294,540, 3,507,660, British Pat. Nos. 1,012,495, 1,022,878, 1,179,290, 1,198,450, Japanese Pat. Application (OPI) Nos. 117414/75, 59025/75, U.S. Pat. Nos. 2,739,891, 2,823,123, 3,068,101, 3,415,649, 3,666,478, 3,756,828, British Pat. No. 1,397,218, U.S. Pat. Nos. 3,133,816, 3,441,413, 3,475,174, 3,545,974, 3,726,683, 3,843,368, Belgian Patent 731,126, British Pat. Nos. 1,138,514, 1,159,825, 1,374,780, Japanese Patent Publication Nos. 378/65, 379/65, 13822/68, U.S. Pat. Nos. 2,271,623, 2,288,226, 2,944,900, 3,253,919, 3,671,247, 3,772,021, 3,589,906, 3,666,478, 3,754,924, West German Pat. application (OLS) No. 1,961,638, etc.

The light-sensitive material of the present invention may contain a dispersion of water-insoluble or slightly soluble synthetic polymer for the purpose of improving dimensional stability, etc. For example, there can be used homo- or copolymers of alkyl (meth)acrylates, alkoxyalkyl (meth)acrylates, glycidyl (meth)acrylate, (meth)acrylamide, vinyl ester (e.g., vinyl acetate), acrylonitrile, olefins, styrene, etc., or polymers containing as monomer components combination of the above-described ones and acrylic acid, methacrylic acid, $\alpha,\beta$-unsaturated dicarboxylic acid, hydroxyalkyl (meth)acrylate, sulfoalkyl (meth)acrylate, styrenesulfonic acid, or the like. As such polymers, there can be used, for example, those described in U.S. Pat. Nos. 2,376,005, 2,739,137, 2,853,457, 3,062,674, 3,411,911, 3,488,708, 3,525,620, 3,607,290, 3,635,715, 3,645,740, British Pat. Nos. 1,186,699, 1,307,373, etc. Contrasty emulsions as in the present invention are suited for reproduction of line images and, since dimensional stability is of importance in such use, incorporation of the above-described polymer dispersion is preferred.

In the process of the present invention, imagewise exposed silver halide photographic light-sensitive materials can be photographically processed in a conventional manner.

Processing solutions can be conventional except the developer. Either of development processing forming only silver images (black-and-white photographic processing) or color photographic processing may be used depending on the end use. Processing temperature is usually selected from between 18° C. and 50° C., but temperatures of lower than 18° C. or higher than 50° C. may also be employed.

In the case of black-and-white photographic processing, the developer can contain known developing agents. As such compounds, there are illustrated 3-pyrazolidones (e.g., 1-phenyl-3-pyrazolidone), aminophenols (e.g., N-methyl-p-aminophenol, etc.), 1-phenyl-3-pyrazoline, dihydroxybenzenes (e.g., hydroquinone, etc.), etc. These compounds may be used in combination. In particular, developers containing dihydroxybenzenes are preferred. The developer containing a dihydroxybenzene as a sole developing agent is particularly preferred.

In addition, the developer generally contains a known preservative, alkali agent, pH buffering agent, antifogging agent, etc., and, if necessary, it may contain a dissolving aid, toning agent, development accelerator, surface active agent, defoaming agent, water softener, hardening agent, viscosity-imparting agent, etc.

The process of the present invention enables one to obtain gamma higher than 10 even when developing with a developer containing not less than about 0.15 mol/l sulfite ion. The pH of the developer to be used in the process of the present invention is preferably about 10.5 to 12.3. If the pH exceeds 12.3, the developer becomes so unstable even when the sulfite ion concentration is high that it is difficult to maintain photographic properties stable for longer than 3 days.

As the fixing solution, that with a generally used composition can be used. As fixing agents, there can be used thiosulfates, thiocyanates and, in addition, organic sulfur compounds known to exhibit effects as fixing agents. The fixing solution may contain water-soluble aluminum salts or the like as hardener.

The present invention will now be illustrated in more detail by reference to the following Examples.

EXAMPLE 1

To an aqueous gelatin solution maintained at 50° C. were simultaneously added a silver nitrate aqueous solution and a potassium bromide aqueous solution over 30 minutes, during which the pAg was kept at 8.0. Thus, there was prepared a silver bromide emulsion having a mean particle size of 0.22μ. After removal of soluble salts in a conventional manner, this emulsion was chemically ripened at 60° C. for 75 minutes by adding sodium thiosulfate in an amount of 48 mg per mol of silver bromide. This emulsion contained 100 g gelatin per mol of silver bromide. To the resulting silver bromide emulsion was added each of the compounds of the present invention, comparative compound (a) of 1-formyl-2-p-tolylhydrazide, and comparative compound (b) of 1-formyl-2-(4-acetamidophenyl)hydrazide (from Japanese Patent Application (OPI) No. 16623/78) as shown in Table 1 and, further, 5-methylbenzotriazole ($2 \times 10^{-3}$ mol/mol Ag), 4-hydroxy-6-methyl-1,3,3a,7-tetrazaindene ($7 \times 10^{-3}$ mol/mol Ag), a dispersion of polyethyl acrylate (20 g/mol Ag), and 2-hydroxy-4,6-dichloro-1,3,5-triazine sodium salt (1 g/mol Ag) were added thereto, then coated on cellulose triacetate film in a silver amount of 48 ml/100 cm². Each sample was exposed for 1 second under an optical wedge.

In order to examine changes in photographic properties (sensitivity and gamma) in the effect of changing the degree of stirring the developer, samples were developed for 5 minutes at 20° C. under the following three stirring conditions using a developing tank (content volume: 5 l) designed to bubble nitrogen gas from the bottom of the tank so as to stir the developer, then subjected to ordinary processings (stopping, fixing, washing with water, and drying).

Stirring Condition (A)

The system was stirred for 5 seconds from immediately after initiation of the development by introducing the nitrogen stream (flow rate: 200 ml/min), then allowed to stand.

Stirring Condition (B)

The system was stirred for 5 seconds by introducing a nitrogen stream and then allowed to stand for a subsequent 15 seconds. The sequence was repeated alternately for 5 minutes.

Stirring Condition (C)

The system was stirred throughout development. The developer had the following composition.

| Developer | |
|---|---|
| N-Methyl-p-aminophenol Hemisulfate | 5 g |
| Hydroquinone | 10 g |
| Anhydrous Sodium Sulfite | 75 g |
| Sodium Metaborate Tetrahydrate | 30 g |
| Polyethylene Glycol (mean molecular weight: 1,500) | 1 g |
| Potassium Hydroxide | 12 g |
| Water to make | 1 l |

The photographic properties thus obtained are shown in Table 1.

In Table 1, relative sensitivities are of reciprocals of exposure amounts necessary to obtain a density of 1.5 excluding fog, and are based using the value of sample No. 6 developed under stirring condition (B) (marked by an asterisk *) as 100.

As is shown in Table 1, when comparative compounds a and b (from Japanese Patent Application (OPI) No. 16623/78, etc.) were used, sensitivity and gamma were seriously changed depending upon the degree of stirring the developer. On the other hand, the use of compounds of the present invention reduced the changes in sensitivity and gamma, and good reproducibility of sensitivity and gamma was obtained even when stirring was greatly varied. That is, substantially consistant photographic properties (sensitivity and gamma) are easily obtained employing any developing process (automatic developing machines based on different stirring methods, dish-developing process, etc.). In addition, the amount of the compound of the present invention is extremely less than that required of comparative compound (a) or (b).

TABLE 1

| Sample No. | Compound | Amount (g/mol AgBr) | Stirring Condition (A) Sensitivity | γ | Stirring Condition (B) Sensitivity | γ | Stirring Condition (C) Sensitivity | γ |
|---|---|---|---|---|---|---|---|---|
| 1 | Comparative Compound (a) | 3.3 | 138 | 20 | 110 | 17 | 75 | 12 |
| 2 | Comparative Compound (b) | 4.8 | 130 | 18 | 105 | 15 | 80 | 12 |
| 3 | (21) | 0.048 | 82 | 20 | 85 | 20 | 90 | 20 |
| 4 | (25) | 0.060 | 88 | 17 | 90 | 18 | 95 | 18 |
| 5 | (12) | 0.044 | 85 | 20 | 95 | 20 | 100 | 20 |
| 6 | (10) | 0.041 | 98 | 18 | 100* | 19 | 103 | 19 |
| 7 | (1) | 0.029 | 100 | 20 | 105 | 20 | 112 | 20 |
| 8 | (31) | 0.099 | 70 | 14 | 80 | 15 | 83 | 15 |
| 9 | (24) | 0.054 | 91 | 18 | 95 | 18 | 97 | 18 |
| 10 | (18) | 0.14 | 108 | 18 | 116 | 18 | 121 | 19 |

EXAMPLE 2

In manner analogous to Example 1, there were prepared large-sized (30.5 cm × 25.4 cm) samples, and exposed through a 150-line gray contact screen so as to uniformly give 50% dots, followed by developing according to the following two developing processes.

Development I (dish development)

Place 5 l of a developer in a developing dish and develop at 27° C. for 1 minute and 40 seconds with no stirring.

Development II (automatic developing machine)

Develop at 27° C. for 1 minute and 40 seconds using an automatic developing machine, model FG-24 Pakorol, made by Fuji Photo Film. Co., Ltd.

The composition of the developer was as follows

| Developer | |
|---|---|
| Hydroquinone | 15 g |
| Anhydrous Sodium Sulfite | 40 g |
| Potassium Carbonate | 70 g |
| Potassium Bromide | 1 g |
| Polyethylene Glycol (mean molecular weight: 1,500) | 1 g |
| 5-Nitroindazole | 30 mg |
| Boric Acid | 8 g |
| Potassium Hydroxide | 18 g |
| Water to make | 1 l |

Unevenness of development was visually rated according to the following four grades A to D.

A: No uneven places were observed.
B: A few uneven places were observed.
C: Many uneven places were observed.
D: Large and many uneven places were observed.

Grades A and B are practically acceptable while grades C and D are practically unacceptable.

As is shown in Table 2, the compounds of the present invention caused almost no unevenness of development both in the processing using the automatic developing machine and in the dish development.

On the other hand, when the comparative compounds were used, unevenness of development was so serious in the dish development that they cannot be practically used, through processing using the automatic developing machine caused unevenness of development within practically acceptable degree.

TABLE 2

| Sample No. | Compound | Development I | Development II |
|---|---|---|---|
| 1 | Comparative Compound (a) | B | C |
| 2 | Comparative Compound (b) | B | C-D |
| 3 | (21) | A | B |
| 7 | (1) | A | A |
| 6 | (10) | A | A |
| 5 | (12) | A | A |
| 8 | (31) | A | B |

While the invention has been described in detail and with reference to specific embodiments thereof, it will be apparent to one skilled in the art that various changes and modifications cna be made therein without departing from the spirit and scope thereof.

What is claimed is:

1. A silver halide photographic light-sensitive material having at least one silver halide photographic emulsion layer comprising substantially surface latent image silver halide grains, and containing in said photographic emulsion layer or at least one of other hydrophilic colloid layers a compound represented by the following general formula (I):

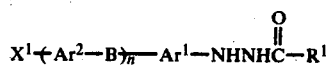

wherein $X^1$ represents a group containing a

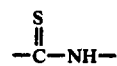

moiety, $Ar^1$ and $Ar^2$ each represents a substituted or unsubstituted aromatic group, B represents a divalent linking group, n is 0 or 1, and $R^1$ represents a hydrogen atom, an unsubstituted alkyl group, or a substituted or unsubstituted aryl group.

2. The photographic light-sensitive material of claim 1, wherein $X^1$ represents

wherein $R^2$ represents a substituted or unsubstituted aliphatic group, a substituted or unsubstituted aromatic group, or a substituted or unsubstituted heterocyclic ring group, $R^3$ represents a hydrogen atom, or a substituted or unsubstituted aliphatic group, $R^4$ represents a hydrogen atom, a substituted or unsubstituted aliphatic group, or a substituted or unsubstituted aromatic group provided that at least one of $R^3$ and $R^4$ represents a hydrogen atom, and $R^2$ and $R^3$ may combine to form a ring.

3. The photographic light-sensitive material of claim 1, wherein $X^1$ represents

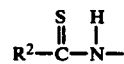

wherein $R^2$ represents a substituted or unsubstituted aliphatic group, a substituted or unsubstituted aromatic group, or a substituted or unsubstituted heterocyclic ring group.

4. The photographic light-sensitive material of claim 1, wherein $X^1$ represents

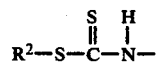

wherein $R^2$ represents a substituted or unsubstituted aliphatic group, a substituted or unsubstituted aromatic group, or a substituted or unsubstituted heterocyclic ring group.

5. The photographic light-sensitive material of claim 1, wherein $X^1$ represents

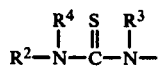

wherein $R^2$ represents a substituted or unsubstituted aliphatic group, a substituted or unsubstituted aromatic group, or a substituted or unsubstituted heterocyclic ring group, $R^3$ represents a hydrogen atom, or a substituted or unsubstituted aliphatic group, $R^4$ represents a hydrogen atom, a substituted or unsubstituted aliphatic group, or a substituted or unsubstituted aromatic group provided that at least one of $R^3$ and $R^4$ represents a hydrogen atom, and $R^2$ and $R^3$ may combine to form a ring.

6. The photographic light-sensitive material of claim 1, wherein $R^1$ represents a hydrogen atom, a straight chain or branched chain unsubstituted alkyl group having 1 to 3 carbon atoms, or a substituted or unsubstituted phenyl group.

7. The photographic light-sensitive material of claim 6, wherein $R^1$ represents a hydrogen atom, a methyl group or a substituted or unsubstituted phenyl group.

8. The photographic light-sensitive material of claim 2, 3, 4, or 5, wherein $R^2$ represents a substituted or unsubstituted straight chain, branched chain or cyclic alkyl group, an alkenyl group, an alkynyl group, a substituted or unsubstituted phenyl group, a substituted or unsubstituted naphthyl group or a substituted or unsubstituted 5- or 6-membered saturated or unsaturated heterocyclic ring containing 1 to 4 hetero atoms.

9. The photographic light-sensitive material of claim 2 or 5, wherein $R^3$ represents a hydrogen atom, a substituted or unsubstituted straight chain, branched chain or cyclic alkyl group, an alkenyl group or an alkynyl group.

10. The photographic light-sensitive material of claim 2 or 5, wherein $R^4$ represents a hydrogen atom, a substituted or unsubstituted straight chain, branched chain or cyclic alkyl group, an alkenyl group, an alkynyl group, a substituted or unsubstituted phenyl group, or a substituted or unsubstituted naphthyl group.

11. The photographic light-sensitive material of claim 2 or 5, wherein $R^2$ and $R^3$ combine to form a ring of the formula:

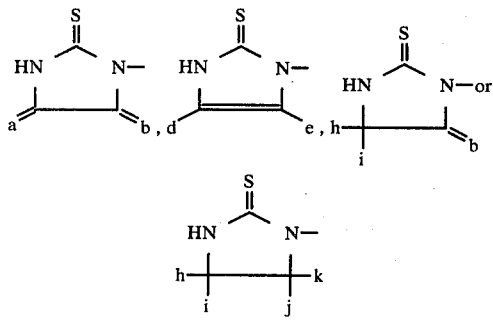

wherein a and b each represents O, S, or a divalent group of

and d, e, f, g, h, i, j and k each represents a hydrogen atom, or an alkyl group or an aryl group which may be substituted.

12. The photographic light-sensitive material of claim 1, wherein $Ar^1$ and $Ar^2$, each represents a substituted or unsubstituted phenylene group or a substituted or unsubstituted naphthylene group.

13. The photographic light-sensitive material of claim 1, wherein n is 0.

14. The photographic light-sensitive material of claim 1, wherein n is 1.

15. The photographic light-sensitive material of claim 1, 2, 3, 4, or 5, wherein $R^1$ represents a hydrogen atom.

16. The photographic light-sensitive material of claim 2 or 5, wherein $R^3$ and $R^4$ represent hydrogen atoms.

17. The photographic light-sensitive material of claim 1, wherein said substantially surface latent image silver halide grain is a silver halide which provides a greater sensitivity when developed with a surface developer than when developed with an internal developer.

18. The photographic light-sensitive material of claim 1, wherein said silver halide emulsion is a monodisperse emulsion.

19. The photographic light-sensitive material of claim 1, wherein said compound of the formula (I) is present in said photographic emulsion layer.

20. The photographic light-sensitive material of claim 1, wherein said compound of the formula (I) is present in an amount of about $10^{-8}$ to $10^{-2}$ mol per mol of silver halide.

21. The photographic light-sensitive material of claim 1, wherein said compound of the formula (I) is present in an amount of about $10^{-6}$ to $10^{-3}$ mol per mol of silver halide.

22. The photographic light-sensitive material of claim 1, wherein said silver halide has a mean particle size of not more than about 0.7 micron and is present in a binder wherein the binder is present in an amount of not more than 250 g per mol of silver halide.

23. The photographic light-sensitive material of claim 1, wherein said silver halide emulsion additionally contains a dispersion of a water-insoluble or slightly soluble synthetic polymer.

24. The photographic light-sensitive material of claim 1, wherein said silver halide emulsion additionally contains an iodide in an amount of about $10^{-4}$ to $10^{-2}$ mol per mol of silver.

25. The photographic light-sensitive material of claim 1, wherein said photographic light-sensitive material contains a polyalkylene oxide or a derivative thereof having a molecular weight of 600 or more.

26. The photographic light-sensitive material of claim 25, wherein said photographic light-sensitive material contains a polyalkylene oxide or a derivative thereof in an amount of about $5 \times 10^{-4}$ g to 5 g per mol of silver halide.

27. A process for forming photographic images which comprises developing the photographic light-sensitive material of claim 1 using a developer containing not more than about 0.15 mole per liter sulfite ion and having a pH of about 10.5 to 12.3.

28. The process of claim 27, wherein development is carried out in the presence of a polyalkylene oxide or a derivative thereof having a molecular weight of 600 or more.

29. The process of claim 27, wherein the developing solution contains a polyalkylene oxide or a derivative thereof having a molecular weight of 600 or more.

30. The process of claim 29, wherein the developing solution contains a polyalkylene oxide or a derivative thereof in an amount of about $1 \times 10^{-2}$ g to 40 g per liter of the developer.

* * * * *